United States Patent [19]

Reiff et al.

[11] 4,012,362

[45] Mar. 15, 1977

[54] POLYMERS CONTAINING 8-HYDROXYQUINOLINE GROUPS

[75] Inventors: Günther Reiff, Rua Poul Harris, Brazil; Dieter Margotte, Krefeld-Bockum, Germany; Karstel Idel, Krefeld, Germany; Hugo Vernaleken, Krefeld-Bockum, Germany; Dieter Freitag, Krefeld-Traar, Germany

[73] Assignee: Bayer Aktiengesellschaft, Germany

[22] Filed: May 2, 1975

[21] Appl. No.: 573,837

Related U.S. Application Data

[63] Continuation-in-part of Ser. No. 549,276, Feb. 12, 1975, abandoned.

[30] Foreign Application Priority Data

Feb. 15, 1974 Germany ........................ 2407307
Feb. 15, 1974 Germany ........................ 2407306

[52] U.S. Cl. .................... 260/47 UA; 75/101 BE; 75/117; 75/119; 75/120; 260/2.2 R; 260/283 R; 526/307; 75/121

[51] Int. Cl.² ....................................... C08F 120/60

[58] Field of Search ... 260/47 UA, 283 R, 88.1 PA, 260/88.3 R, 2.2 R; 526/307; 75/101 BE, 117, 119, 120, 121

[56] References Cited

UNITED STATES PATENTS

| 2,530,774 | 1/1951 | Kehe et al. ........................ 260/283 |
| 3,391,114 | 7/1968 | Schaefer et al. ..................... 260/47 |

*Primary Examiner*—Donald Levy
*Assistant Examiner*—Peter F. Kulkosky
*Attorney, Agent, or Firm*—Connolly and Hutz

[57] ABSTRACT

Homo- and copolymers of monomers obtained by acylation of 2-[4-hydroxy(or amino)phenyl]-2-[5-(8-hydroxyquinolyl)]-propane with $\alpha,\beta$-monoolefinically unsaturated carboxylic acid halides or - anhydrides. As comonomers can be employed compounds containing one or more $\alpha,\beta$-olefinically unsaturated groups such as olefines, diolefines, acrylic acid derivatives, vinyl monomers. The polymers having molecular weights between 5000 – 500,000 can be prepared by radical or ionic chain mechanisms, in continuous or discontinuous processes. They may be used for removing metal ions from their solution, for complexing of interfering metallic impurities in thermoplastic or thermosetting resins or in form of their metal complexes as stabilizers for plastics.

3 Claims, No Drawings

POLYMERS CONTAINING 8-HYDROXYQUINOLINE GROUPS

This application is a continuation-in-part application of copending application Ser. No. 549,276, filed Feb. 12, 1975, and now abandoned.

The invention relates to polymers which contain 8-hydroxyquinoline groups, and to the use of these polymers as complex-forming agents for metal ions and as stabilisers for plastics. Further uses will be apparent from the description.

It is known to employ 8-hydroxyquinoline as a complex-forming agent for metals in analytical chemistry, since it forms inner complexes, so-called oxinates, which can be precipitated quantitatively, with numerous metal ions (compare R. Berg "Die analytische Verwendung von o-Oxychinolin ("Oxin") and seiner Derivate") ("The use of o-hydroxyquinoline ("oxine") and of its derivatives in analysis"), 2nd edition, Stuttgart 1938 and R. Bock, Angew. Chemie 67, 420 (1955)). In addition, 8-hydroxyquinoline exhibits powerful fungicidal and antiseptic effects. 8-Hydroxyquinoline is a compound which is readily soluble in customary solvents.

It is the object of the present invention to fix 8-hydroxyquinoline to organic macromolecules, whilst preserving the complex-forming action and the other properties characteristic of 8-hydroxyquinoline. Such products are intended to be used in industrial or commercial processes for removing and complexing metal ions from solutions or, in a combination with metal ions, as stabilisers for plastics or, where appropriate, in plant protection or in antiseptic compositions.

The object has been achieved by alkylating 8-hydroxyquinoline with p-isopropenylphenols or p-isopropenylanilines, and reacting the alkylation product with α,β- unsaturated carboxylic acids having 3–5 C-atoms or their derivatives, to give polymerisable monomers, and converting these polymerisable monomers into homopolymers or copolymers.

According to the invention there is provided a process for the preparation of monomers of the formula I comprising acylation 2-[4-hydroxy-phenyl]-2-[5-(8-hydroxyquinolyl)]-propane or 2-[4-aminophenyl]-2-[5-(8-hydroxyquinolyl)]- propane with acid halides of the formula

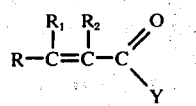

wherein
R denotes H, —COOH or COOR$_3$ [wherein R$_3$ denotes C$_1$–C$_{18}$ alkyl or cycloalkyl, preferably C$_1$–C$_8$-alkyl (branched or linear) or cyclohexyl],
R$_1$ denotes —H or —CH$_3$,
R$_2$ denotes —H or —CH$_3$, and
Y denotes —Cl or —Br
or with acrylic anhydride, methacrylic anhydride crotonic anhydride or maleic anhydride.

The compounds which serve as the starting material, namely 2-[4-hydroxyphenyl]-2-[5-(8-hydroxyquinolyl)]-propane and 2-[4-aminophenyl]-2-[5-(8-hydroxyquinolyl)]-propane do not form a subject of the present invention. They can be obtained by reaction of p-isopropenylphenol or p-isopropenylaniline with 8-hydroxyquinoline in the presence of suitable catalysts, in solution or in bulk, as can be seen in detail from the examples.

The acylation of the abovementioned amine or phenol can be carried out at temperatures of 0° to 100° C in bulk, in solution or by interphase reaction. Preferably, the acylation is carried out in an inert solvent such as methylene chloride, dichloroethane, chloroform, monochlorobenzene, dichlorobenzene, benzene, toluene or nitromethane.

If carboxylic acid halides, such as carboxylic acid chlorides or carboxylic acid bromides, preferably carboxylic acid chlorides, are employed, it is advisable to carry out the reaction in the presence of a hydrogen halide acceptor. This can be an alkali metal hydroxide, an alkali metal carbonate, an alkali metal acetate, a tert. amine such as pyridine, quinoline, isoquinoline, triethylamine or diethylaniline, or their mixtures. The hydrogen halide acceptor can be employed in an equivalent amount or in 1–50 times the equivalent amount, based on carboxylic acid halides.

Where carboxylic acid anhydrides are used, the acylation can be carried out in bulk or in the abovementioned solvents, under the same temperature conditions. Here, hydrogen halide acceptors are not necessary though it is frequently advantageous to carry out the acylation in the presence of small amounts (up to about 10% by weight, based on anhydride) of a tert. amine such as pyridine, concentrated sulphuric acid, zinc chloride or alkali metal acetates.

It is surprising, when carrying out the process according to the invention, that the 8-hydroxyl group in the quinoline does not undergo the acylation reaction.

Where the acylation is carried out in bulk with carboxylic acid anhydrides, the monomers according to the invention are obtained directly and can, if desired, be recrystallised from alcohols or aromatic hydrocarbons, such as benzene, and aliphatic hydrocarbons, such as petroleum ether. If the acylation is carried out in solvents with carboxylic acid halides or carboxylic acid anhydrides, the organic phase can be isolated, washed with acidified water and then with water, and concentrated.

It is also possible first to concentrate the organic phase, dilute it with fresh solvent, then wash it with acidified water and thereafter with water until neutral, and remove the organic solvent by distillation.

According to the invention there are provided polymers with average molecular weight of about 5,000 to 500,000, which comprise recurring polymerised units of a monomer of the formula I

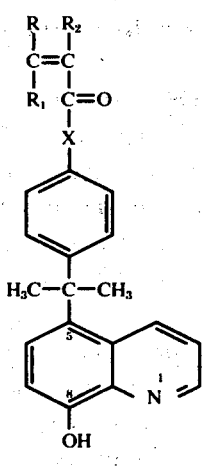

wherein
X denotes —O— or —NH—;
R denotes H, -COOH or -COOR₃ [with R₃ = C₁ – C₁₈ — (linear or branched)-alkyl or cycloalkyl],
R₁ denotes H or CH₃ and
R₂ denotes H or CH₃ or contain these units in a copolymerized form.

Preferably, R and R₁ denote H, R₂ denotes H or CH₃ and R₃ denotes C₁ – C₈ alkyl or cyclohexyl. The preferred average molecular weights are 10,000 to 100,000.

In the present application, polymers are understood to include homopolymers and copolymers, and the end groups can be formed by the radicals of the initiators or regulators used in any particular case.

The term copolymer comprises not only copolymers with a statistical distribution of the copolymerised monomers and block copolymers, but also graft copolymers, where monomers are grafted onto a previously formed homopolymer or copolymer. Statistical copolymers are preferred.

As comonomers, one or more monomers from the following groups can be employed for the copolymerisation with at least one monomer of the formula I:
a. α,β-Monoolefines with 2–4 C atoms, such as ethylene, propylene, butene-1 and isobutylene.
b. Conjugated diolefines with 4–6 C atoms, such as butadiene, isoprene, 2,3-dimethylbutadiene and 2-chlorobutadiene.
c. Acrylic acid and methacrylic acid, acrylonitrile and methacrylonitrile, acrylamide and methacrylamide, acrylic acid alkyl esters and methacrylic acid alkyl esters with 1–18, preferably 1–8, C atoms in the alcohol component, such as methyl acrylate, ethyl acrylate, propyl acrylate, isopropyl acrylate, n-butyl acrylate, 2-ethylhexyl acrylate, stearyl acrylate and the corresponding methacrylic acid alkyl esters.
d. Vinyl esters of organic monocarboxylic acids wherein the acid component contains 1–18, preferably 2–4 C atoms, such as vinyl acetate and vinyl propionate.
e. Monoolefinically unsaturated halogenohydrocarbons, preferably vinyl chloride or vinylidene chloride.
f. Vinylaromatics such as styrene, o- or p-methylstyrene, α-methylstyrene, α-methyl-p-isopropylstyrene, α- methyl-m-isopropylstyrene or p-chlorostyrene, but preferably styrene.

In this category, the monomers which polymerise less readily, such as α-methylstyrene and m- and p-isopropyl-α-methylstyrene are preferably always employed as a mixture with at least one other of the copolymerisable monomers mentioned.

g. Monoesters of α,β-monoolefinically unsaturated monocarboxylic acids, with 3–4 C atoms, and dihydric saturated aliphatic alcohols with 2–4 C atoms, such as 2-hydroxyethyl methacrylate, 2-hydroxypropyl methacrylate, 4-hydroxybutyl methacrylate, 2-hydroxyethyl acrylate, 2-hydroxypropyl acrylate and 4-hydroxybutyl acrylate.

h. N-Methylol ethers of acrylamide and methacrylamide, of the general formula II $$CH_2=C-CO-N-CH_2-OR_2 \quad \text{II}$$
$$\phantom{CH_2=C-CO-}|\phantom{CO-N-}|$$
$$\phantom{CH_2=C-CO-N-}R\phantom{-CO-N-}R_1$$

in which
R represents hydrogen or methyl,
R₁ represents hydrogen, alkyl, aralkyl or aryl, and
R₂ represents alkyl or cycloalkyl, such as methyl, ethyl, n-propyl, isopropyl, n-butyl, isobutyl or cyclohexyl (compare German Auslegeschrift (German Published Specification) 1,035,363).

The N-methylol methyl ether of methacrylamide is preferred. The monomers of group h) are employed, and incorporated into the copolymer, in amounts of 1–20% by weight, based on the total monomers.

i. Diesters and monoesters of maleic acid, fumaric acid and itaconic acid with 1–18 C atoms in the alcohol component, and also maleic anhydride, maleic acid or fumaric acid, amides of maleic acid and fumaric acid, malemides and unsaturated copolymerisable polyesters which contain the radicals of maleic acid and/or fumaric acid as polymerisable constituents.

j. Vinyl alkyl ethers with 1–4 C atoms in the alkyl group, such as vinyl methyl ether, vinyl ethyl ether, vinyl propyl ether and vinyl butyl ether.

k. Monomers which have a crosslinking action and contain several non-conjugated olefinically unsaturated carbon-carbon bonds, such as divinylbenzene, diallyl phthalate, divinyl adipate, acrylic acid allyl ester and/or methacrylic acid allyl ester, methylene-bis-acrylamide, methylene-bis-methacrylamide, triallyl cyanurate, triallyl isocyanurate, triacryloyl-perhydro-S-triazine, bis-acrylates and bis-methacrylates of glycols or polyglycols with 2–20 C atoms, such as ethylene glycol diacrylate or dimethacrylate, propylene glycol diacrylate or dimethacrylate, butylene glycol 1,4-diacrylate or 1,4-dimethacrylate, tetraethylene glycol diacrylate or dimethacrylate and tris-acrylates and tris-methacrylates of trimethylolpropane and glycerol.

The crosslinking monomers of group k) are preferably employed for the copolymerisation in amounts of 0.1–12% by weight, based on total monomers. They are incorporated into the copolymer in the same amounts.

In addition, primary, secondary or tertiary aminoalkyl esters of acrylic acid or methacrylic acid with, preferably, 2–4 C atoms in the alkyl group, and glycidol acrylate or methacrylate, can also be employed as comonomers and can, if desired, be crosslinked, during or after the copolymerisation, via the amino or epoxide group, respectively.

Preferably, comonomers of groups (c) and (f) in combination with comonomers of group (k) are employed for the copolymerisation.

The comonomers can — unless stated otherwise — be employed for the copolymerisation in amounts of 5 to 95% by weight, preferably 50 to 90% by weight, based on total monomers. Correspondingly, the monomers of the formula I account for 5 – 95% by weight, preferably 50 to 10% by weight. They are also preferentially incorporated into the copolymers in these proportions. If, in addition to the customary comonomers, comonomers of groups (h) and (k), or yet other monomers copolymerisable with the monomers of the formula I, are also employed, their proportion shown under (h) and (k) is contained in the total proportion of the comonomers (5–95% by weight).

The homopolymers and copolymers can be prepared by radical or ionic chain mechanisms, in continuous or discontinuous processes.

In the case of the ionic polymerisation, catalysts of the anionic reaction type are preferably employed, in amounts of 0.01–5% by weight, preferably 0.01–2% by weight, based on total monomers; examples are metal alkyls, alkali metal alcoholates, metal amides or metal hydroxides, such as butyllithium, zinc alkyl with 1 – 4 C atoms in the alkyl groups, lithium alcoholate, potassium tert.-butylate, sodium amide or mixed catalysts, such as aluminum triethyl/titanium-IV chloride, used in aprotic solvents, such as, for example, dimethylformamide, dimethylaniline, benzene or toluene, at temperatures of about −80° C to approx. +110° C, preferably at −60° C to +10° C, if appropriate under pressure.

Preferably, the polymerisation takes place in accordance with the radical chain mechanism, in the presence of substances which yield free radicals.

Suitable substances of this type are inorganic per-compounds, such as potassium persulphate or ammonium persulphate, hydrogen peroxide, alkali percarbonates, organic peroxide compounds, such as acyl peroxides, for example dibenzoyl peroxide, dichlorobenzoyl peroxide, di-tert.-butyl peroxide and dicumyl peroxide, alkyl hydroperoxides, such as tert. butyl hydroperoxide, cumyl hydroperoxide and p-menthane hydroperoxide, organic percarbonates such as cyclohexyl peroxydicarbonate, diisopropyl peroxydicarbonate and ethylhexyl peroxydicarbonate, and also tert.-butyl peroctoate, tert.-butyl perpivalate and azodiisobutyronitrile. It is also possible to employ inorganic or organic per-compounds in combination with reducing agents, in a manner which is in itself known. Examples of suitable reducing agents are sodium pyrosulphite or sodium bisulphite, sulphinates, iron-II salts, cobalt naphthenate, ascorbic acid and aromatic amines such as p-toluidine.

Metal complexes, such as acetylacetonates of manganese and cobalt, and diacyl peroxide/tert. amine systems, are also suitable. However, the polymerisation can also be initiated by elevated temperatures, light rays and high energy rays.

Preferably, the copolymerisation is carried out with radical-forming substances such as azodiisobutyronitrile, benzoyl peroxide or potassium persulphate/sodium sulphite.

The amount of catalyst which can be used lies within the limits usually involved, that is to say approximately between 0.01 and 5% by weight, preferably between 0.01 and 2% by weight, calculated relative to the total monomers employed.

The polymerisation can be carried out at temperatures of −20° to 160° C, preferably at 60° to 110° C, if appropriate under pressure, in accordance with the customary methods of bulk polymerisation, solution polymerisation, precipitation polymerisation, dispersion polymerisation, emulsion polymerisation or bead polymerisation. Dispersion polymerisation and bead polymerisation, which — after separation from the dispersing medium — give the polymers in a form where they are immediately ready to use, are preferred. Solution polymerisation is particularly preferred.

If polymerisation is carried out in solution, the customary solvents are employed. Alcohols, such as ethanol to n-butanol, iso-butanol and tert.-butanol, halogenated hydrocarbons such as methylene chloride, trichloroethylene and tetrachloroethane, ketones such as acetone and methyl ethyl ketone, esters such as ethyl acetate to octyl acetate, ethylglycol acetate and methylglycol acetate, ethylene glycol mono-methyl or bis-methyl ether, diethylene glycol mono-methyl or bis-methyl ether and aromatic hydrocarbons such as toluene, benzene, xylene, dichlorobenzene and trichlorobenzene. The high polymers can be isolated either by steam-stripping or by precipitation in a non-solvent such as petroleum, benzines, petroleum ether or methanol. They can also be isolated on screw evaporators. Further, the solutions can be isolated by spray-drying or drying in a thin layer evaporator, tube evaporator or falling film evaporator.

The precipitation polymerisation is preferably carried out in a good solvent for the monomer in which, however, the polymer is insoluble, such as, for example, in methanol or fluorochlorohydrocarbons, such as dichlorofluoromethane.

The dispersion polymerisation or bead polymerisation is carried out in an aqueous liquor in the presence of the customary protective colloids such as methylcellulose, gelatine, saponified polyvinyl acetate, styrene-maleic anhydride polymers, precipitated calcium phosphate or aluminum hydroxy gels. In addition, buffer substances such as sodium carbonate, prim-, sec- or tert-sodium phosphate and alkali metal borates can be added. In order to control the particle diameter, extraneous salts such as sodium sulphate, or alcohols such as butanol, can be present in amounts of 0.1 to 2% by weight, based on monomers.

The particle diameter can also be regulated by co-use of surface-active substances, such as fatty alcohol sulphonates or polyethylene oxides in which phenols were used as the starter (reaction products of phenols with ethylene oxide) and the like.

It is important to adjust the average molecular weight, and this can be done with the aid of 0.1 to 2% by weight, relative to total monomers, of a chain transfer agent. These agents are mercaptans, such as tert.-dodecylmetcaptan, xanthates, thioglycerol, nitrotoluenes, cumene, halogen derivatives such as carbon tetrachloride, haloforms such as chloroform, methyl vinyl carbinol, allyl alcohol and the like. The regulators are employed in such amounts that average molecular weights of 5,000 to 500,000 result. After the dispersion polymerisation or bead polymerisation the particles of diameter 10 $\mu$ to 2 mm are separated from the aqueous liquor and washed and dried. Thereafter they are, in most cases, in a free-flowing form.

The polymers, carrying 8-hydroxyquinoline groups, can be used, in the solid form or dissolved in organic solvents, for removing metal ions of the transition elements of the periodic system of the elements, that is to say of the elements Sc to Zn (atomic number 21 to 30), Y to Cd (atomic numbers 39–48), La to Hg (atomic numbers 57–80), Ac to U (atomic numbers 89–92) and of magnesium, calcium, aluminum, lead, tin and bismuth, from solutions. To improve the absorptive capacity of the particles, the latter can be swollen before use, for example with xylene or toluene. The absorption of the metal ions is reversible. The metal ions can again be removed by elution with strong acids or bases or stronger complex-forming agents such as acetylacetonates and complexones such as nitrilotriacetic acid. The polymers described are therefore of particular interest for the removal of traces of heavy metals from industrial effluents or process sewage.

The polymers according to the invention can also be employed for the complexing of interfering metallic impurities in thermoplastics or thermosetting resins, in amounts of 0.01 to 10% by weight, based on the total mixture. Thus, as is known, iron impurities in polyvinyl chloride lower the heat stability, but the latter can be improved by complexing with the polymers described.

The polymers according to the invention can also be used, in the form of their metal complexes, for example with cadmium, tin or lead, as stabilisers for plastics. Such plastics are polyvinyl chloride or its copolymers, such as ethylene/vinyl chloride or vinyl acetate/vinyl chloride copolymers, or polyethylene, polypropylene, polyacrylates, copolymers of acrylates or methacrylates and at least one further monomer, vinyl acetate polymers, ethylene/vinyl acetate copolymers, polycarbonates, polysulphones, polyphenylene oxides, styrene copolymers, polymers of the ABS type (acrylonitrile-butadiene-styrene graft polymer thermoplastics), polyamides of the nylon type or polycaprolactam, polycaprolactam, polyethylene terephthalates, polyacetals and the like. The heat stability, weathering resistance, stress cracking and sensitivity to hydrolysis can be improved, or influenced, by addition of the polymers according to the invention.

The percentages in the examples are by weight, unless stated otherwise. The average molecular weights are always determined by membrane osmometry.

The starting materials described below, and their manufacture, do not form a subject of the present application.

Preparation of the starting material,
2-[4-hydroxyphenyl]-
2-[5-(8-hydroxyquinolyl)]-propane.

1,508 of 8-hydroxyquinoline, 483 g of p-isopropenylphenol and 150 g of bentonite (acid catalyst K 20 from Messrs. Suedchemie, Munich) are brought together and heated to 180° C for 24 hours in a nitrogen atmosphere under reflux. The reaction mixture is then filtered through a pressure filter to separate off the solid catalyst.

After addition of methylene chloride/water, a part of the 2-[4-hydroxyphenyl]-2-[5-(8-hydroxyquinolyl)]-propane is obtained in a crystalline form. The mixture which remains is subjected to a steam distillation, whereby the 8-hydroxyquinoline employed in excess can be recovered. On renewed addition of methylene chloride, a further part of the functional hydroxyquinoline is obtained in a crystalline form.

The two crystalline fractions, when combined, give a total yield of 460 g (46% of theory). After extraction with benzene in a Soxhlet, colourless crystals of melting point 139° C are obtained from benzene.

| Analysis: | C | H | N |
|---|---|---|---|
| calculated | 77.4% | 6.10% | 5.01% |
| found | 77.5% | 6.03% | 4.87% |

Preparation of the starting material:
2-[4-methacryloyloxyphenyl]-
2-[5-(8-hydroxyquinolyl)]-propane 279 g of 2-[4-hydroxyphenyl]-2-[5-(8-hydroxyquinolyl)]-propane are introduced into 1,120 ml of methylene chloride and a solution of 190.8 g of sodium carbonate in 1,000 ml of water together with 3.0 ml of triethylamine is added dropwise at 13° C. 110 g of methacrylic acid chloride and 200 ml of methylene chloride are then added over the course of 20 minutes.

The mixture is stirred for a further 20 minutes and the organic phase is separated off and washed once with dilute HCl and then with water until neutral. After concentrating the organic phase in vacuo, 180 g (52% of theory) of the methacrylic acid ester of 2-[4-methacryloyloxyphenyl]-2-[5-(8-hydroxyquinolyl)]-propane are obtained from ethanol as colourless crystals of melting point 141° C.

| Analysis: | C | H | N |
|---|---|---|---|
| calculated | 76.06% | 6.09% | 4.03% |
| found | 75.6% | 6.05% | 3.94% |

Preparation of the starting material:
2-[4-aminophenyl]-2-[5-(8-hydroxyquinolyl)]-propane 2,180 g of 8-hydroxyquinoline, 400 g of p-isopropenylaniline and 300 g of bentonite (acid catalyst K 20 from Messrs. Suedchemie, Munich) are heated for 26 hours to 160° C under reflux in a nitrogen atmosphere. The reaction mixture is filtered through a pressure filter and then successively subjected first to a vacuum distillation and then to a steam distillation. This results in almost quantitative recovery of the 8-hydroxyquinoline employed in excess. Methylene chloride is then added to the reaction mixture and the organic phase is separated off. The residue remaining after concentrating the organic phase is extracted with a methylene chloride/petroleum ether mixture and 382 g (46% of theory) of 2-[4-aminophenyl]-2-[5-(8-hydroxyquinolyl)]-propane of melting point 105–107° C are obtained. Crystallisation from ethanol raises the melting point of the colourless crystals to 109° C.

| Analysis: | C | H | N |
|---|---|---|---|
| calculated | 77.7% | 6.46% | 10.02% |
| found | 77.5% | 6.58% | 9.88% |

Preparation of the starting material
2-[4-methacrylamidophenyl]-2-[5-(8-hydroxyquinolyl)]-propane 200 g of 2-(4-aminophenyl)-2-[5-(8-hydroxyquinolyl)]-propane are dissolved in 200 ml of methylene chloride and 500 ml of pyridine. 75.0 g of methacrylic acid chloride in 1,000 ml of methylene chloride are slowly added dropwise to this solution. The mixture is left to stand for 15 hours at room temperature and the solvents are then removed in vacuo. The residue is taken up in methylene chloride and washed twice with 1 N $H_2SO_4$ and then with water. After concentrating the organic phase, 205 g (80.5% of theory) of 2-[4-methacrylamidophenyl)]-2-[5-(8-hydroxyquinolyl)]-propane are obtained in the form of colourless crystals of melting point 126–127° C from benzene/petroleum ether.

| Analysis: | C | H | N |
|---|---|---|---|
| calculated | 76.5% | 6.30% | 8.11% |
| found | 76.3% | 6.18% | 8.02% |

EXAMPLE 1

Homopolymerisation in toluene

To a 50 percent strength solution of 100 g of 2-[4-methacryloyloxyphenyl]-2-[5-(8-hydroxyquinolyl)]-propane in toluene and 1% by weight of tert. dodecylmercaptan, relative to the monomer, are added dropwise 2% by weight of dibenzoyl peroxide, relative to the monomer, dissolved in toluene, at 100° C over the course of 3 to 4 hours. Thereafter the mixture is stirred for a further 4 hours at 100° C. The vinyl polymer is then either precipitated in methanol or poured out onto a metal sheet and dried in a vacuum drying cabinet. The average molecular weight Mn determined osmometrically was 19,500. Nitrogen analysis: calculated 4.03%, found 3.92%.

EXAMPLE 2

Copolymerisation with methacrylic acid methyl ester

To a 50 percent strength solution of 20 g of 2-[4-methacryloyloxyphenyl]-2-[5-(8-hydroxyquinolyl)]-propane and 80 g of methyl methacrylate in toluene and 2% by weight of tert. dodecylmercaptan, relative to the monomer, are added dropwise 2% by weight of dibenzoyl peroxide, relative to the monomers, on toluene, at 100° C over the course of 3 to 4 hours. Thereafter the mixture is stirred for a further 4 hours at 100° C. The vinyl polymer is then either precipitated in methanol or poured out onto a metal sheet and dried in a vacuum drying cabinet. The average molecular weight of the statistical copolymer was determined osmometrically. Mn = 37,000, nitrogen analysis: calculated 0.8%, found 0.78%.

EXAMPLE 3

Copolymerisation with styrene

To a 50 percent strength solution of 10 g of 2-[4-methacryloyloxyphenyl]-2-[5-(8-hydroxyquinolyl)]-propane and 90 g of styrene in benzene and 2% by weight of tert. dodecylmercaptan, relative to the monomers, are added dropwise 2% by weight of dibenzoyl peroxide, relative to the monomers, in benzene, at 80° C over the course of 3 to 4 hours. Thereafter the mixture is stirred for a further 4 hours at 80° C. The vinyl polymer is then either precipitated in methanol or poured out onto a metal sheet and dried in a vacuum drying cabinet. The average molecular weight of the statistical copolymer was determined osmometrically and was 42,000. Nitrogen analysis: calculated 0.40%, found 0.38%.

EXAMPLE 4

Bead polymerisation 150 g of styrene, 12 g of divinylbenzene, 2 g of dibenzoyl peroxide and 50 g of 2-[4-methacryloyloxy-phenyl-]-2[-5-(8-hydroxyquinolyl)]-propane are dispersed in 1,000 ml of water, 40 ml of toluene and 2 g of polyvinyl alcohol. This mixture is heated to 80° C for 5 hours with vigorous stirring and is then stirred for a further 8 hours at 100° C oil bath temperature and allowed to cool slowly. The bead polymer is filtered off, washed with water and dried in a vacuum drying cabinet at 80° C. The softening point of this crosslinked polymer is above 360° C.

The product is crosslinked and practically insoluble in all solvents so that it was not possible to determine the molecular weight. Nitrogen analysis: calculated 0.95%, found 0.93%.

EXAMPLE 5

Terpolymerisation with styrene and acrylonitrile 61.0 g of distilled styrene, 16.0 g of destabilised acrylonitrile and 23 g of 2-[4-methacryloyloxyphenyl]-2-[8-hydroxyquinolyl)]-propane are dissolved in chlorobenzene. 2 g of dibenzoyl peroxide in chlorobenzene are then added dropwise to the reaction mixture over the course of 3 hours at 100° C. The mixture is stirred for a further 4 hours and thereafter the polymer is precipitated in alcohol or the solvent is removed and the polymer dried in vacuo. The osmometrically determined molecular weight is 31,900. Nitrogen analysis: calculated: 6.37%, found: 6.29%.

EXAMPLE 6

90 g of styrene and 10.0 g of 2-[4-methacrylamidophenyl]-2-[5-(8-hydroxyquinolyl)]-propane are dissolved in toluene together with 2% by weight of tert. dodecylmercaptan, relative to the monomers, and the solution is heated to 100° C. 2 g of dibenzoyl peroxide in toluene are added dropwise over the course of 2 to 3 hours to this reaction mixture and the reaction is allowed to continue for a further 6 hours. Thereafter, the product is either precipitated in alcohol or dried after removal of the solvent in a vacuum drying cabinet. The average molecular weight was determined osmometrically. Mn = 26,200. Nitrogen analysis: calculated: 0.81; found: 0.8%.

EXAMPLE 7

50 ml of 20% strength sodium hydroxide solution, followed by 40 g of acrylic acid, are added to 10 g of 2-[4-methacryloyloxyphenyl] -2-[5-(8-hydroxyquinolyl)]-propane in 150 ml of ethanol, whilst stirring. 0.7 g of potassium peroxydisulphate as the initiator is added and the reaction mixture is heated to 70° C. The reaction is allowed to continue for a further 4 hours and is then discontinued. The polymer which precipitates on cooling the reaction solution is filtered off and dried. The average molecular weight was determined osmometrically and is 5,900. Nitrogen analysis: calculated: 0.72; found: 0.68%.

EXAMPLE 8

5 g of the polymer described in Example 2 in 60 ml of methylene chloride are stirred with 0.85 g of mercury-(II) acetate for 8 hours at room temperature. In the course thereof, a red colour develops. Analysis of the polymer: 10.2% of mercury.

The mother liquor contains 0.24 mg/l ≙ 0.24 ppm of mercury.

EXAMPLE 9

3 g of the polymer described in Example 2 are dissolved in 150 ml of methylene chloride and the solution is shaken with 180 ml of an 0.1% strength by weight mercury-II acetate solution for 3 hours. The phases are then separated and the mercury content of the aqueous phase is determined.

Residual content of Hg: 0.7 mg/l ≙ 0.7 ppm of Hg.

EXAMPLE 10

4 g of the polymer described in Example 2 are dissolved in 200 ml of methylene chloride and the solution is shaken with 0.42 g of copper-II acetate for 4 hours. The reaction solution is filtered and the residue which remains after removing the solvent is analysed. Copper content of the polymer: 2.9%.

EXAMPLE 11

4 g of the polymer described in Example 7 are dissolved in a water/ethanol solvent mixture and the solution is shaken with 0.53 g of $CuSO_4 \cdot 5H_2O$ for 2 hours. After filtration, the solvent is removed and the residue which remains is examined for its copper content. Copper content of the polymer: 3.4%.

EXAMPLE 12

4 g of the polymer described in Example 2 are dissolved in 100 ml of methylene chloride and the solution is shaken with 81 ml of an 0.5% strength by weight nickel-II acetate solution for 4 hours. After separating the phases, the organic phase is brought to dryness and analysed. Nickel content of the polymer: 1.6%.

EXAMPLE 13

4 g of the polymer described in Example 2 are dissolved in 200 ml of methylene chloride and the solution is shaken with 1.01 g of lead-IV acetate for 4 hours. The solution is then filtered and concentrated. The lead content of the polymer was found to be 4.7%.

EXAMPLE 14

0.75 g of a vinyl polymer containing mercury, prepared analogously to Example 8 and having a mercury content of 3.1%, is dissolved in 30 ml of methylene chloride and the solution is shaken with a solution of 0.3 g of potassium cyanide in 30 ml of water for 8 hours. The decolourisation of the polymer containing metal, which occurs during this treatment, indicates re-complexing. The organic phase is isolated and dried over sodium sulphate. It is then precipitated in petroleum ether and the product is dried in vacuo at 80° C. Residual mercury content in the polymer: 0.3% of Hg.

EXAMPLE 15

2 g of a vinyl polymer containing lead, prepared analogously to Example 13 and having a lead content of 1.0%, are dissolved in 100 ml of methylene chloride and the solution is shaken with 50 ml of 0.1 N $HNO_3$ for 6 hours. The organic phase is then separated off, washed until neutral and dried over sodium sulphate. The solvent is stripped off and the residue is examined for its lead content. Only traces of lead remained detectable in the polymer. Lead content of the polymer: Pb < 0.05%.

We claim:

1. Polymers of number of average molecular weights of about 5,000 to 500,000, which comprise recurring polymerised units of a monomer of the formula I

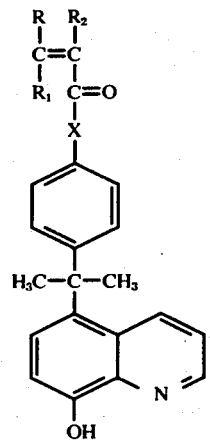

wherein
X denotes O or NH;
R denotes H, —COOH or —$COOR_3$,
$R_1$ denotes H or $CH_3$,
$R_2$ denotes H or $CH_3$ and
$R_3$ denotes $C_1$–$C_{18}$-(linear or branched)-alkyl or cycloalkyl or contain these units in a copolymerised form.

2. Polymers according to claim 1, characterised in that they consist of
  A. 5–95% by weight of copolymerised units of monomers of the formula I and
  B. 95–55% by weight of copolymerised units of at least one of the monomers styrene, acrylonitrile, methacrylonitrile, acrylic acid, methacrylic acid, acrylamide, methacrylamide, acrylic acid esters or methacrylic acid esters with 1–8 C atoms in the alcohol component, 2-hydroxyalkyl acrylates or methacrylates with 2–3 C atoms in the alkyl group, diesters and monoesters of maleic acid, fumaric acid or itaconic acid with 1–18 C atoms in the alcohol component, vinyl alkyl ethers with 1–4 C atoms in the alkyl group, vinyl chloride, vinylidene chloride, vinyl esters of organic monocarboxylic acids with 2–4 C atoms in the acid component, α,β-monoolefines with 2–4 C atoms or conjugated diolefines with 4–6 atoms.

3. Polymers according to claim 2, characterised in that 0.1–12% by weight of the copolymerised units of the monomers
  B. consist of copolymerised units of at least one of the monomers divinylbenzene, diallyl phthalate, divinyl adipate, acrylic acid allyl ester or methacrylic acid allyl ester, methylene-bis-acrylamide, methylene-bis-methacrylamide, triallyl (iso)cyanurate, and bis-acrylates or bis-methacrylates of glycols or polyglycols with 2–20 C atoms.

* * * * *